(12) United States Patent
Walsh

(10) Patent No.: US 8,323,911 B2
(45) Date of Patent: Dec. 4, 2012

(54) HIGH THROUGHPUT ASSAY FOR DISCOVERING NEW INHIBITORS OF THE GIRK1/4 CHANNEL

(75) Inventor: Kenneth B. Walsh, Blythewood, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 13/107,351

(22) Filed: May 13, 2011

(65) Prior Publication Data
US 2011/0281278 A1 Nov. 17, 2011

Related U.S. Application Data

(60) Provisional application No. 61/395,449, filed on May 13, 2010.

(51) Int. Cl.
*G01N 33/53* (2006.01)
(52) U.S. Cl. ........................................................ 435/7.2
(58) Field of Classification Search .................. None
See application file for complete search history.

(56) References Cited

U.S. PATENT DOCUMENTS
2008/0227819 A1* 9/2008 Struenker et al. ............ 514/332

OTHER PUBLICATIONS

Nobles et al. (2010) Pfluegers Archiv. 460: 99-108.*
Morimoto et al. (2007) Molec. Pharacol. 71: 1075-1088.*
Claycomb et al., "HL-1 Cells: A Cardiac Muscle Cell Line That Contracts and Retains Phenotypic Characteristics of the Adult Cardiomyocyte", Proceedings of the National Academy of Sciences of the United States of America, vol. 95, No. 6, Mar. 1998, pp. 2979-2984.
Walsh et al., "Neonatal Rat Cardiac Fibroblasts Express Three Types of Voltage-Gated K+ Channels: Regulation of a Transient Outward Current by Protein Kinase C", American Journal of Physiology Heart and Circulatory Physiology, vol. 294, No. 2, Feb. 2008, pp. H1010-H1017.
White et al., "Cardiac Physiology at the Cellular Level: Use of Cultured HL-1 Cardiomyocytes for Studies of Cardiac Muscle Cell Structure and Function", American Journal of Physiology Heart and Circulatory Physiology, vol. 286, No. 3, Mar. 2004, pp. H823-H829.
Zhang et al., "A Simple Statistical Parameter for Use in Evaluation and Validation of High Throughput Screening Assays", Journal of Biomolecular Screening, vol. 4, No. 2, Apr. 1999, pp. 67-73.

* cited by examiner

*Primary Examiner* — Michael Pak
(74) *Attorney, Agent, or Firm* — Dority & Manning, P.A.

(57) ABSTRACT

In certain embodiments of the present disclosure, a method for determining an inhibitor of acetylcholine-activated potassium channel is described. The method includes incubating a cardiac cell in a solution comprising a test compound. The method further includes adding a muscarine (M2) receptor agonist to the cardiac cell in the solution and monitoring the cardiac cell for a change in membrane potential. A statistically insignificant change in the membrane potential following addition of the muscarine (M2) receptor to the solution signifies that the test compound is a $K^+$ channel blocker that inhibits opening of the acetylcholine-activated potassium channel.

13 Claims, 8 Drawing Sheets

Control

Carbachol

BaCl$_2$ 100 pA
20 ms

HIGH THROUGHPUT ASSAY FOR DISCOVERING NEW INHIBITORS OF THE GIRK1/4 CHANNEL

CROSS-REFERENCE TO RELATED APPLICATION

The present application is based on and claims priority to U.S. Provisional Application Ser. No. 61/395,449 having a filing date of May 13, 2010, which is incorporated by reference herein.

BACKGROUND

The acetylcholine-activated $K^+$ channel ($I_{K,Ach}$) is a member of the superfamily of proteins known as the G-protein-coupled inward rectifier $K^+$ (GIRK) channels. GIRK channels function as cellular mediators of a wide range of hormones and neurotransmitters and are expressed in cardiac muscle, skeletal muscle, neurons, and endocrine tissue. The cardiac $I_{K,Ach}$ is composed of the inward rectifier $K^+$ (Kir) channel subunits Kir3.1 and Kir3.4 (GIRK1/4), which are arranged in a tetramer. In the heart, binding of muscarinic agents such as acetylcholine or carbachol to the muscarinic (M2) receptor causes a dissociation of the βγ subunits of the G inhibitory protein (Gi), which subsequently bind to and activate $I_{K,Ach}$. Once opened, $I_{K,Ach}$ allows the movement of $K^+$ out of the cardiac myocyte, causing the cell membrane potential to become more negative.

Cardiac arrhythmias are defined as abnormalities in the generation or conduction of electrical impulses in the heart. Atrial fibrillation (AF) is a rapid and irregular atrial muscle arrhythmia that results in erratic and incomplete cardiac contractions. AF is the most prevalent arrhythmia in the United States, affecting more than 2 million adult patients. The frequency of AF increases with age, occurring in 3% to 5% of those older than 65 years of age and 9% of people older than 80 years. Regardless of the underlying cardiac disease, chronic AF is associated with increased morbidity and mortality. Current antiarrhythmic drugs used in the treatment of AF are limited by suboptimal efficacy and a high incidence of toxicity. One novel target for AF drug therapy is the GIRK1/4 channel. Recent studies indicate that $I_{K,Ach}$ is constitutively active in patients with AF. This constitutively active channel causes the atrial action potential duration to shorten with a resulting increase in cell excitability. Therefore, GIRK1/4 channel blockers, by decreasing atrial excitability, should reduce the incidence of AF. However, discovery of new drugs that bind to and block the cardiac $I_{K,Ach}$ has been hampered by the absence of a cell-based screening assay that uses the GIRK1/4 channel.

As such, methods to determine new drugs that bind to and inhibit $I_{K,Ach}$ would be desirable. An assay system that is capable of detecting such new drugs would be particularly beneficial.

SUMMARY

Aspects and advantages of the disclosure will be set forth in part in the following description, or may be obvious from the description, or may be learned through the practice of the disclosure.

In certain embodiments of the present disclosure, a method for determining an inhibitor of acetylcholine-activated potassium channel is described. The method includes incubating a cardiac cell in a solution comprising a test compound. The method further includes adding a muscarinic (M2) receptor agonist to the cardiac cell in the solution and monitoring the cardiac cell for a change in membrane potential. A statistically insignificant change in the membrane potential following addition of the muscarinic (M2) receptor to the solution signifies that the test compound is a $K^+$ channel blocker that inhibits opening of the acetylcholine-activated potassium channel.

In still other embodiments of the present disclosure, an assay system is described. The assay system includes a structure capable of incubating a cardiac cell in a solution, a muscarinic (M2) receptor agonist, and a detection substance capable of generating a detectable signal upon binding to a cytoplasmic component of the cardiac cell.

These and other features, aspects and advantages of the present disclosure will become better understood with reference to the following description and appended claims.

BRIEF DESCRIPTION OF THE DRAWINGS

A full and enabling disclosure, including the best mode thereof, directed to one of ordinary skill in the art, is set forth more particularly in the remainder of the specification, which makes reference to the appended figures in which.

DETAILED DESCRIPTION

Figure 1A:
FIG. 1A illustrates ion currents recorded during voltage steps applied from a holding potential of −40 mV to −100, −80 and −60 mV under control conditions, in the presence of 10 μM carbachol and following addition of 0.5 mM $BaCl_2$ (solid lines represent zero current) in accordance with certain aspects of the present disclosure.
Figure 1A:
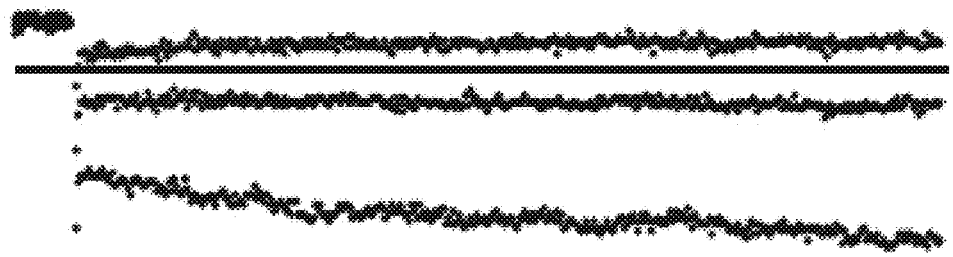
Figure 1A:

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

The present disclosure is generally related to an assay system and method for determining an inhibitor of acetylcholine-activated potassium channel. In accordance with the present disclosure, immortalized cardiac atrial cells, expressing the GIRK1/4 channel, were analyzed using patch-clamp recording procedures and fluorescent imaging plate reader (FLIPR) measurements. Application of carbachol activated a whole-cell $I_{K,Ach}$ current that was blocked by antiarrhythmic agents and the Kir toxin tertiapin. In cells loaded with the membrane potential-sensitive fluorescent dye bis-(1,3-dibutylbarbituric acid) trimethine oxonol ($DiBAC_4(3)$), carbachol caused a rapid, time-dependent decrease in the fluorescent signal. This carbachol-induced decrease in fluorescence was blocked by $BaCl_2$ and enhanced by increasing the driving force for $K^+$ across the cell membrane. The GIRK1/4 channel/$DiBAC_4(3)$ assay was screened against a small-compound library of $Na^+$ and $K^+$ channel modulators. Analogues of propafenone and amiloride were identified as GIRK channel blockers at concentrations less than 1 µM. Thus, the GIRK1/4 channel assay described herein will be useful for expanding the limited pharmacology of $I_{K,Ach}$ blockers and for developing new and selective agents for treating AF.

The present disclosure can be better understood with reference to the following examples.

EXAMPLES

Cell Culture and Plating

The immortalized cardiac HL-1 cell line was generously supplied by Dr. William Claycomb (LSU Medical Center, New Orleans, La.). Cells were maintained in Claycomb/Dulbecco's modified Eagle's medium (DMEM) supplemented with 10% fetal bovine serum (FBS), penicillin/streptomycin, and L-glutamine (Sigma-Aldrich, St. Louis, Mo.). Myocytes were platted on gelatin-coated glass coverslips (5000 cells per coverslip; patch-clamp recording) and in black 96-well plates (25,000 cells per well; FLIPR measurements). Cells were stored in an incubator at 37° C. (5% $O_2$/95% $CO_2$) and used on days 2 to 4 after plating.

Patch-Clamp Recording of IK,Ach Currents

A patch-clamp method was used to record the whole-cell $I_{K,Ach}$ using L/M EPC-7 (Adams & List Associates, Great Neck, N.Y.) and Axopatch 200 (Axon Instruments, Sunnyvale, Calif.) amplifiers. The procedures for measuring cardiac $K^+$ channels have been described in Walsh K B, Zhang J: Neonatal rat cardiac fibroblasts express three types of voltage-gated $K^+$ channels: regulation of a transient outward current by protein kinase C, *Am J Physiol Heart Circ Physiol* 2008; 294:H1010-H1017, incorporated by reference herein. Pipettes were made from borosilicate glass capillaries (World Precision Instruments, Sarasota, Fla.) and had resistances of 1 to 2 Mohms when filled with internal solution. All experiments were conducted on isolated, noncoupled HL-1 cells at room temperature (22-24° C.). For the measurement of $I_{K,Ach}$, cells were placed in a normal Tyrode's solution consisting of 132 mM NaCl, 5 mM KCl, 1 mM $CaCl_2$, 1 mM $MgCl_2$, 5 mM dextrose, and 5 mM HEPES (pH 7.4; with NaOH) (280 mOsm). $I_{Na}$ was blocked with tetrodotoxin (10 µM) and the $Na^+$ channels inactivated by maintaining the myocytes at a holding potential of −40 mV. L-type $Ca^{2+}$ channels were blocked with 500 nM nisoldipine. The internal solution was made from 50 mM KCl, 60 mM $K^+$-glutamate, 2 mM $MgCl_2$, 1 mM $CaCl_2$, 11 mM EGTA, 3 mM adenosine triphosphate (ATP), and 10 mM HEPES (pH 7.3; with KOH) (280 mOsm).

Figure 1B:
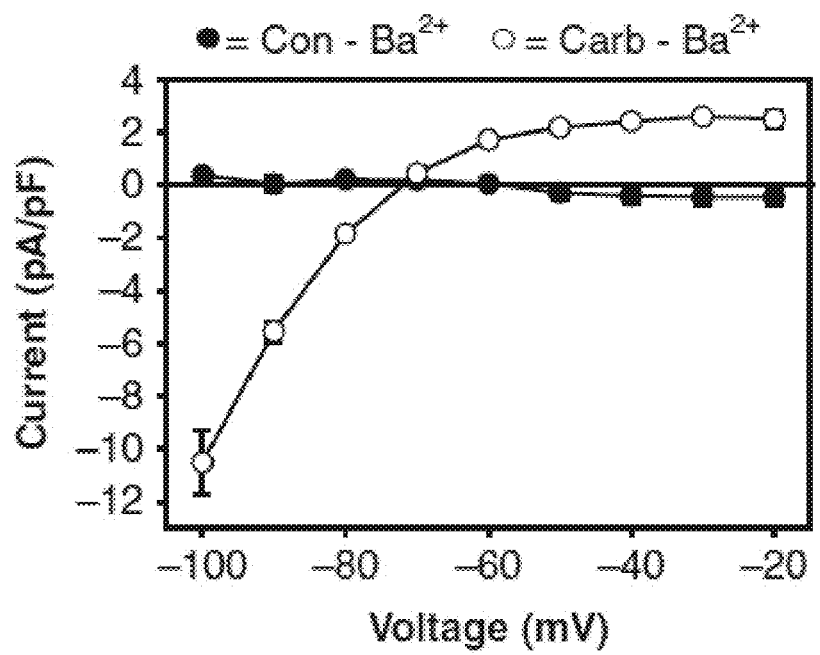
FIG. 1B illustrates the IN relationship for $Ba^{2+}$-sensitive current activated by carbachol (Carb-$Ba^{2+}$) (each point represents the mean±SE of the current measured in 8 cells) in accordance with certain aspects of the present disclosure.
Figure 1C:
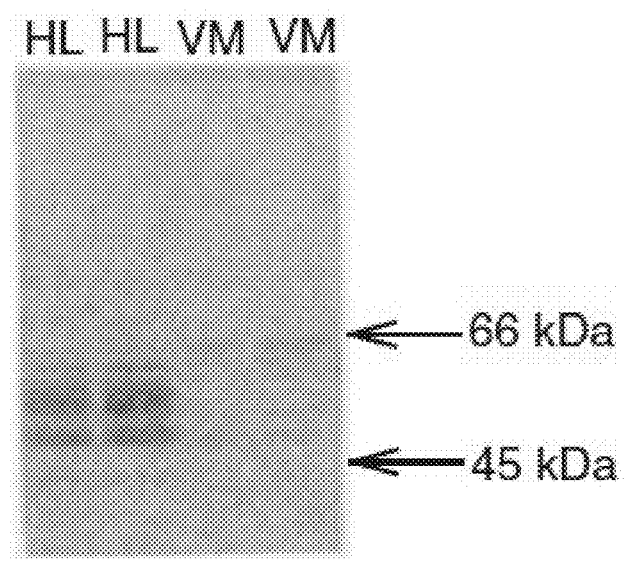
FIG. 1C illustrates an immunoblot obtained with HL-1 cell (HL) and neonatal ventricular myocyte (VM) lysates using an anti-Kir3.1 Ab in accordance with certain aspects of the present disclosure.

Membrane currents were recorded with 12-bit analog/digital converters (Axon Instruments). Data were sampled at 5 KHz and filtered at 1 KHz with a low-pass Bessel filter (Frequency Devices, Ottawa, Ill.). Series resistance was compensated to give the fastest possible capacity transient without producing oscillations. With this procedure, more than 70% of the series resistance could be compensated. Following the measurement of the HL-1 cell background current, $I_{K,Ach}$ was activated by the addition 10 μM carbachol using a rapid perfusion system. $I_{K,Ach}$ was defined as the $BaCl_2$-sensitive current (see FIGS. 1A-1C, illustrating expression of GIRK1/4 channels in HL-1 cells). $I_{K,Ach}$ blockers were added and inhibition determined immediately after carbachol-induced activation. This limited errors in quantifying drug block due to GIRK1/4 channel desensitization and rundown. Averaged current values presented are means±SE.

GIRK1 Subunit Western Blot Analysis

Cell lysates for Western blot analysis were prepared by placing the HL-1 cell cultures into a lysis buffer (50 mM Tris-HCl [pH 7.4], 150 mM NaCl, 50 mM dithiothreitol, 1 mM sodium orthovanadate, 1 mM sodium fluoride, 1 mM phenylmethysulfonyl fluoride, 1 mM EGTA, 0.25% sodium deoxycholate, 2 μg/mL aprotinin, and protease inhibitor cocktail [Roche, Basel, Switzerland]). The protein content of the cell preparations was determined using a protein assay kit (Pierce, Rockford, Ill.). For Western blot analysis of the GIRK1 channel subunit, proteins were separated by electrophoresis on 8% sodium dodecyl sulfate (SDS) polyacrylamide gels using a mini PROTEAN cell (Bio-Rad, Hercules, Calif.). The running buffer contained 25 mM Tris, 193 mM glycine (pH 8.3), and 0.1% SDS. Proteins were transferred to polyvinylidene difluoride membranes using a Trans-Blot apparatus (Bio-Rad). The transfer buffer contained 25 mM Tris, 192 mM glycine (pH 8.5), and 20% methanol. For immunodetection, membranes were blocked in Tris-buffered saline (TBS) containing 0.1% Tween-20, bovine serum albumin, and 0.025% Na-azide for 60 min at room temperature. Antibodies to the Kir3.1 (GIRK1) channel (1:200) (Alomone, Jerusalem, Israel) were incubated with the membranes overnight at 4° C. After primary antibody treatment, the membranes were washed with TBS-0.1% Tween-20 and incubated with a secondary antibody (horseradish peroxidase [HRP]-conjugated rabbit IgG; Cell Signaling Technology, Danvers, Mass.). Immunoreactive bands were visualized on X-ray film (Kodak) using the enhanced chemiluminescence method (Pierce).

GIRK1/4 Channel FLIPR Assay

HL-1 cells were incubated for 1 h in Tyrode's solution containing 5 μM $DiBAC_4(3)$ (AnaSpec, Fremont, Calif.) and fluorescent signals recorded using a Synergy2 microplate reader (BioTek, Winosski, Vt.) at 28° C. Test compounds were dissolved in DMSO at a stock concentration of 10 mM, diluted to various concentrations, and applied to the cells for 5 min prior to the fluorescent measurements. $DiBAC_4(3)$ was present in all experimental solutions. DMSO, up to 1% in Tyrode's solution, had no adverse effects on the cell response. Carbachol or control solution (20 μL) was added to each well (total volume=220 μL) at time zero using the Synergy2 injector system. Data points were collected at 10-s intervals over a 300-s sampling period at excitation and emission wavelengths of 480 and 520 nm, respectively. Positive (carbachol or carbachol+1 mM BaCl2) and negative (water or DMSO) control experiments were performed to calculate Z' factors. The Z' factor is defined as $Z'=1-(3\sigma_P+3\sigma_N)/|\mu_P-\mu_N|$, where $\mu_P$ and $\mu_N$ are the means of the positive control and negative control signals, and σp and $\sigma_N$ are the standard deviations of the positive control and negative control signals, respectively. Plates used for Z' factor determination contained 2 rows each of positive and negative controls. Dose-response curves for selected compounds were obtained and drug potencies determined by fitting the data with the following curve: Max/(1+ $([drug]/IC_{50})^k)$, where the $IC_{50}$ is the concentration of the compound producing a 50% decrease in the maximal carbachol response (Max), and k is the slope factor. Interference of the test compounds with the $DiBAC_4(3)$ fluorescence was determined in the absence of cells by adding various concentrations of the compounds to Tyrode's solution containing the dye.

Drugs and Chemicals

Carbachol, KR-32568, antiarrhythmic agents, and an $Na^+$, $K^+$ channel modulator kit, containing 66 compounds, were purchased from Sigma-Aldrich. The propafenone analogues 1-{2-[3-(tert-butylamino)-2-hydroxypropoxy]phenyl}-3-phenyl-1-propanone, 1-{2-[2-(diethylamino)ethoxy]phenyl}-3-phenyl-1-propanone, 1-{2-[3-(diethylamino)-2-hydroxypropoxy]phenyl}-3-phenyl-1-propanone, 5-hydroxy propafenone, 1-{2-[2-hydroxy-3-(1-piperidinyl)propoxy]phenyl}-3-phenyl-1-propanone, 1-{2-[2-hydroxy-3-(4-morpholinyl)propoxy]phenyl}-3-phenyl-1-propanone, 1-{2-[3-(ethylamino)-2-hydroxypropoxy]phenyl}ethanone, and 1-(1-piperidinyl)-3-(4-propylphenoxy)-2-propanol were obtained from ChemBridge Corp. (San Diego, Calif.).

Results

Measurement of IK,Ach Currents in HL-1 Cells $I_{K,Ach}$ is highly expressed in cardiac sinoatrial nodal, atrioventricular nodal, and atrial tissues. HL-1 cells are an immortalized atrial cell line that displays an adult-like cardiac genotype and contracts spontaneously in cell culture. FIGS. 1A-1C display $I_{K,Ach}$ currents measured in the HL-1 cells using the whole-cell arrangement of the patch-clamp technique. Cells were bathed in normal Tyrode's solution (5 mM $K^+$), and the pipette contained a $KCl/K^+$-glutamate (140 mM $K^+$) solution. Application of carbachol to the recording chamber resulted in the activation of an inward rectifying current (FIGS. 1A-1C). As expected for an inward rectifier $K^+$ channel, the carbachol-activated current was completely blocked by $BaCl_2$ (FIGS. 1A-1C). The reversal potential ($E_{rev}$) for the current (−72 mV) was within range of the calculated Nernst equilibrium potential ($E_K$) (−85 mV) for a $K^+$-selective channel under these conditions.

Figure 2A:
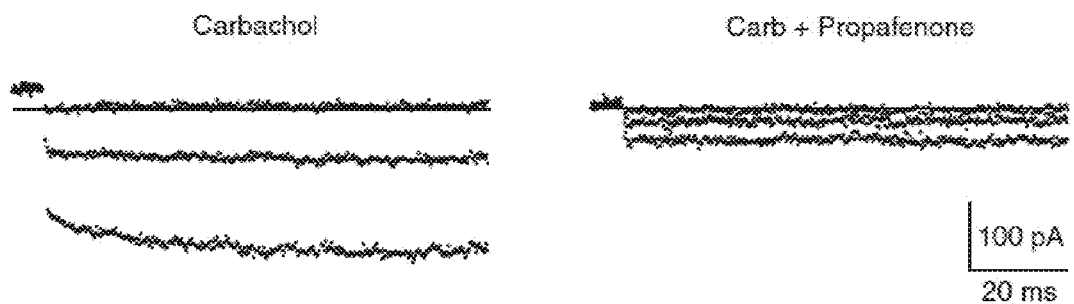
FIG. 2A illustrates pharmacological properties of the HL-1 cell $I_{K,Ach}$ with $I_{K,Ach}$ recorded during voltage steps applied to −100, −80 and −60 mV in the presence of carbachol and following the addition of 10 μM propafenone in accordance with certain aspects of the present disclosure.
Figure 2B:
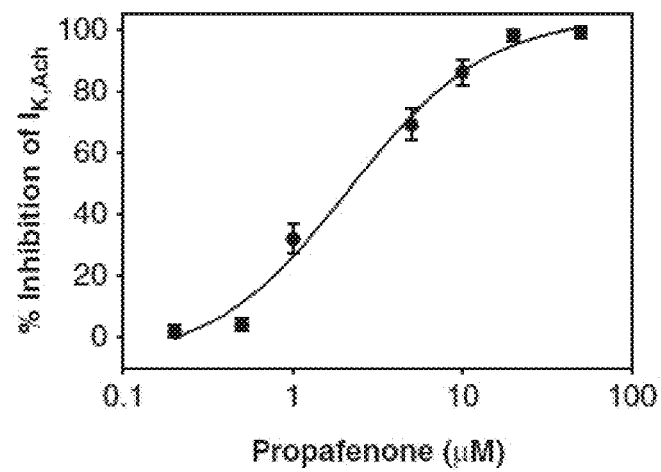
FIG. 2B illustrates a dose response curve for block of $I_{K,Ach}$ measured at −100 mV with propafenone ($IC_{50}$=2 μM) (each point represents the mean±SE inhibition measured in four to six HL-1 cells) in accordance with certain aspects of the present disclosure.
Figure 2C:
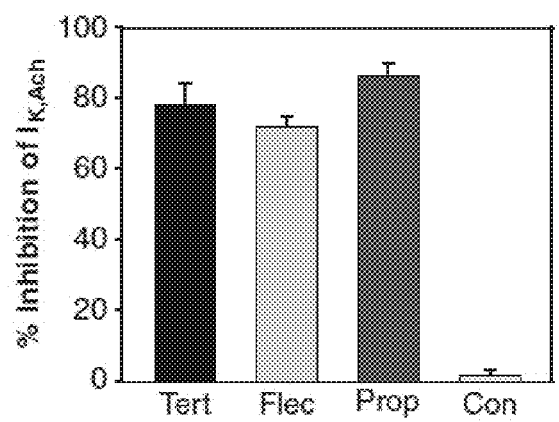
FIG. 2C illustrates percent inhibition of $I_{K,Ach}$ measured at −100 mV with tertiapin (Tert) (100 nM), flecainide (Flec) (100 μM), propafenone (Prop) (10 μM) and control solution (each bar represents the mean±SE inhibition measured in six HL-1 cells) in accordance with certain aspects of the present disclosure.

The cardiac $I_{K,Ach}$ is composed of the inward rectifier Kir3.1 and Kir3.4 (GIRK1 and GIRK4) subunits. As shown in FIGS. 1A-1C, an immunoreactive doublet protein corresponding to the approximately 50- to 55-kDa GIRK1 subunit was identified in HL-1 cells but not in ventricular myocytes using an anti-GIRK1 antibody. The pharmacological properties of the HL-1 cell $I_{K,Ach}$ current were also examined. A number of agents, including the Kir toxin tertiapin (100 nM) and the antiarrhythmic drugs flecainide (100 μM) and propafenone (10 μM), block $I_{K,Ach}$ in primary cultures of adult atrial myocytes. All 3 of these agents strongly blocked 13-15 at the concentrations tested (FIGS. 2A-2C). In contrast, addition of control solution (containing drug vehicle) produced no significant change in the current (FIGS. 2A-2C). The full dose-response curve for the propafenone block of $I_{K,Ach}$ is included in FIGS. 2A-2C. The $IC_{50}$ for the propafenone block was 2 μM. Thus, the inward rectifying current versus voltage relationship, the $Ba^{2+}$-sensitivity and pharmacology of the whole-cell $I_{K,Ach}$ current, and the presence of Kir3.1 subunits are all consistent with the expression of GIRK1/4 channels in the HL-1 cells.

Development of the GIRK1/4 Channel FLIPR Assay

Figure 3:
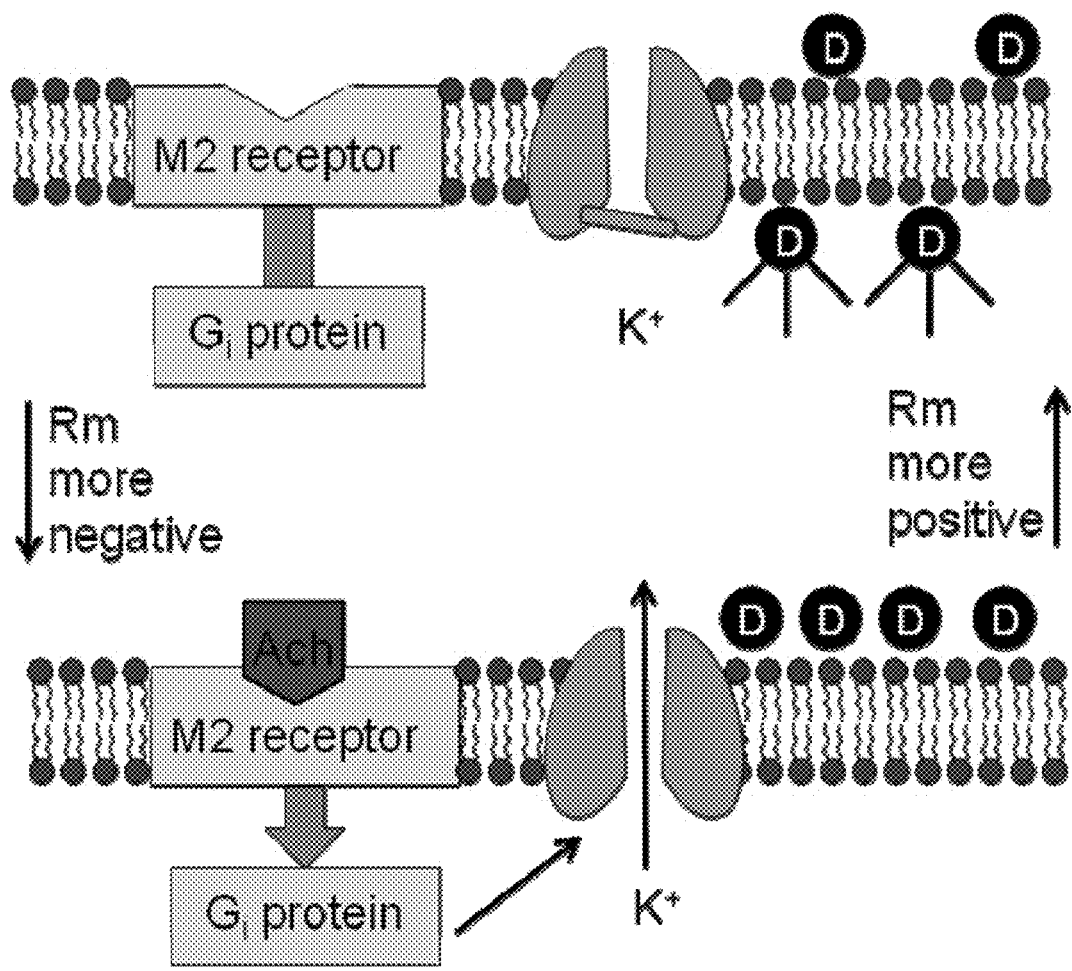
FIG. 3 illustrates an $I_{K,Ach}$ fluorescent assay system in immortalized HL-1 cardiac cells (abbreviations: D=$DiBAC_4$(3), Ach=acetylcholine, Rm=resting membrane potential) in accordance with certain aspects of the present disclosure.

Having demonstrated that the $I_{K,Ach}$ current-GIRK1/4 channel is expressed in the HL-1 cell line, it was determined if these cells could be used for FLIPR measurements of the channel. The experimental design of the screening assay is outlined in FIG. 3. HL-1 cells were cultured in 96-well plates and loaded with the fluorescent membrane potential-sensitive dye $DiBAC_4(3)$. Membrane potential-sensitive dyes such as DiBAC$_4$(3) distribute across the plasma membrane when cells are in the rested state and reach equilibrium (FIG. 3, top panel). The DiBAC$_4$(3) molecules inside the cells become strongly fluorescent upon binding to intracellular proteins and other cytoplasmic components. Treatment of the cells with carbachol activates G$_i$ stimulating the GIRK1/4 channels to open (bottom panel). The resulting efflux of K$^+$ out of the cell should therefore cause the resting membrane potential to become more negative and the DiBAC$_4$(3) molecules to redistribute to the outside of the cell. As a result the cell fluorescent signal should decrease.

Figure 4A:
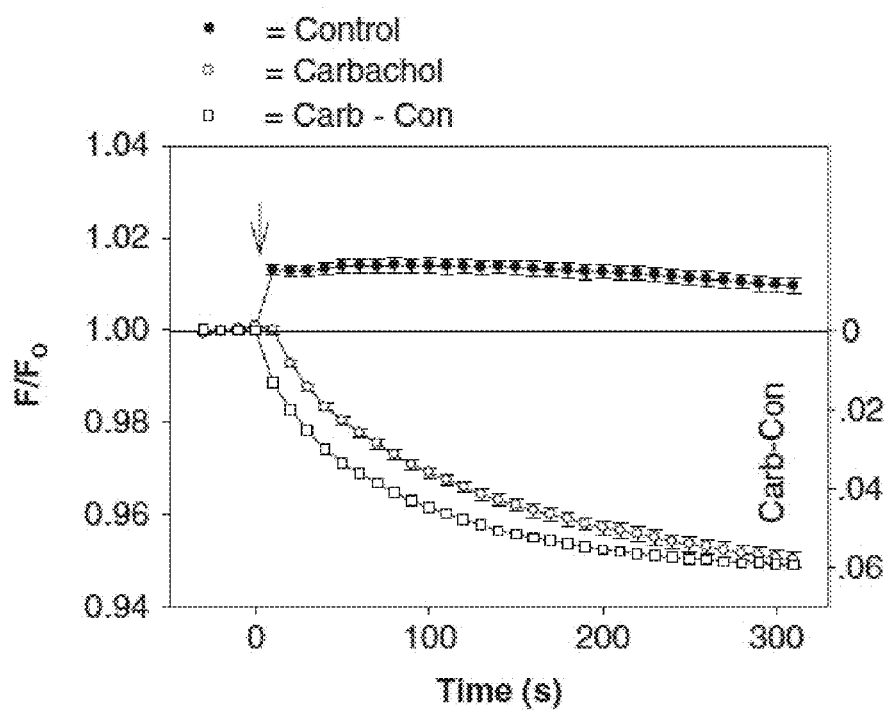
FIG. 4A illustrates development of a GIRK1/4 channel blocker screening assay with $DiBAC_4$(3) fluorescent intensities obtained in HL-1 cells in the presence or absence of carbachol (the ratio of the fluorescent intensity (F/$F_O$) was calculated by dividing the signal in the presence (F) of carbachol (or control solution) by the baseline signal measured before ($F_O$) addition of carbachol (or control solution); each point represents the mean±SE obtained in 6 wells; carbachol was added at time zero (↓)) in accordance with certain aspects of the present disclosure.

The applicability of the GIRK1/4 channel fluorescent assay for drug testing was evaluated in FIGS. 4A-4D. Each figure plots the DiBAC$_4$(3) fluorescence signal measured over time in the 96-well plates using a Synergy2 microplate reader (Biotek). As predicted by the experimental model, addition of carbachol (10 μM) to the cardiac cells caused a rapid, time-dependent decrease in the DiBAC$_4$(3) fluorescent signal (FIG. 4A). In contrast, addition of control solution produced only a small instantaneous rise in the fluorescence. Qualitatively similar results were obtained using the oxonol dye HLB 021-152 (AnaSpec) (results not shown). Comparison of peak fluorescent changes in wells injected with control and carbachol solutions gave Z'-factors ranging from 0.50 to 0.64 (4 plates from two experimental days). The peak carbachol-induced fluorescent signal obtained from these plates was 0.956±0.008 (mean±SD). In order to quantify the GIRK1/4 channel fluorescent signal, the averaged control measurement, obtained in each 96-well plate, was subtracted from the records measured in the presence of carbachol (Carb-Con). This control-subtracted fluorescent signal (i.e. the carbachol-sensitive component) was subsequently obtained and analyzed.

Figure 4B:
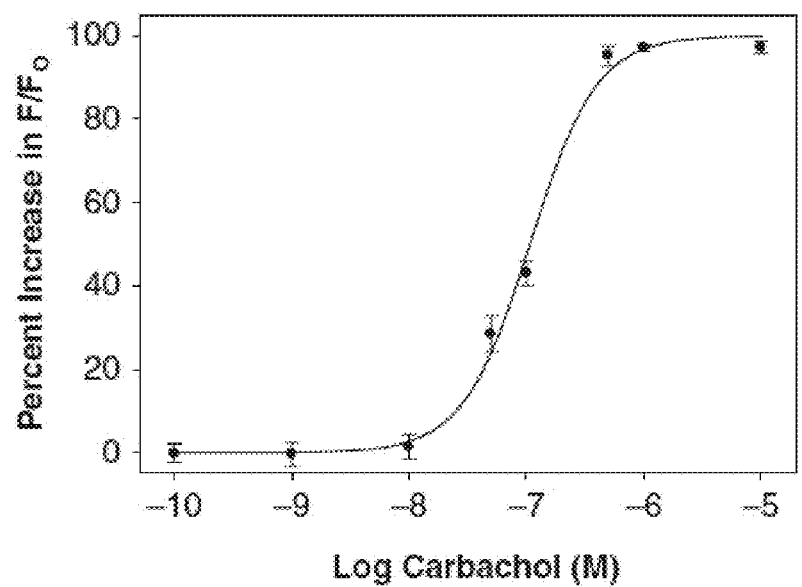
FIG. 4B illustrates a dose-response curve for the carbachol-sensitive fluorescent signal ($EC_{50}$=110 nM) (each point represents the mean±SE of 10 measurements) in accordance with certain aspects of the present disclosure.
Figure 4C:
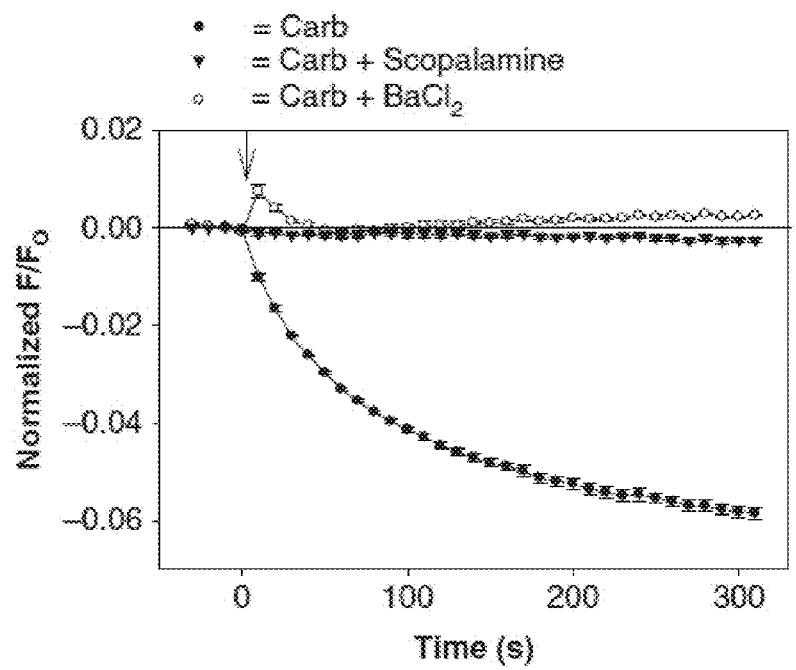
FIG. 4C illustrates a carbachol fluorescent signal measured in HL-1 cells pretreated for 5 min with vehicle solution ($H_2O$) (Carb) and either 1 µM scopolamine or 1 mM $BaCl_2$ (each point represents the mean±SE obtained in 6-8 wells) in accordance with certain aspects of the present disclosure.
Figure 4D:
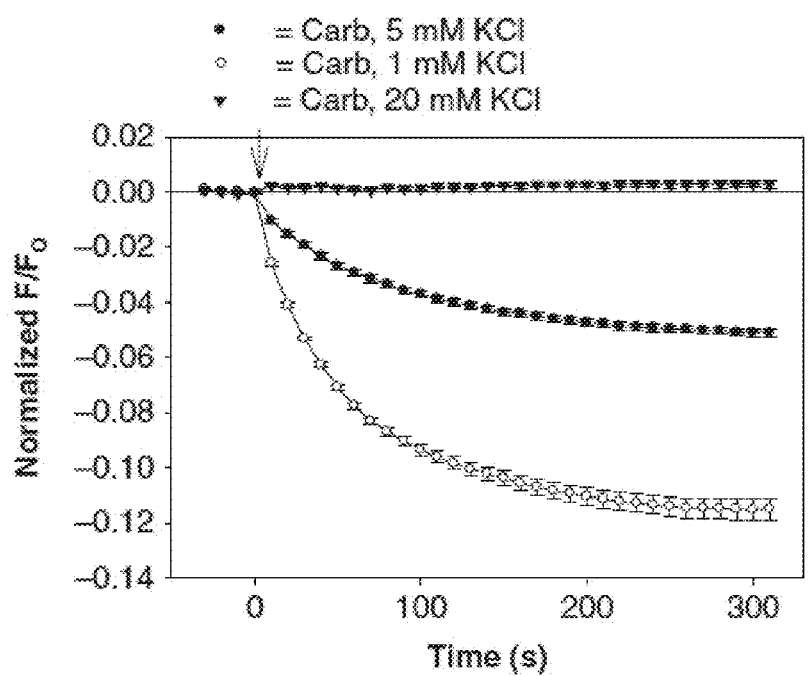
FIG. 4D illustrates a carbachol fluorescent signal measured in HL-1 cells in Tyrode's solutions containing 1 mM, 5 mM and 20 mM KCl (each point represents the mean±SE obtained in 6 wells) in accordance with certain aspects of the present disclosure.

The pharmacological and biophysical properties of the carbachol-sensitive fluorescent signal are summarized in FIGS. 4A-4D. Carbachol activated the GIRK1/4 channel in a concentration dependent manner with a half-maximal effective concentration (EC$_{50}$) of 110 nM (FIG. 4B). The carbachol signal was blocked by 1 mM BaCl$_2$ and inhibited during pretreatment with the muscarinic antagonists scopolamine (1 μM) (FIG. 4C) and atropine (1 μM) (results not shown). The effect of altering the driving force for K$^+$ across the plasma membrane on the GIRK1/4 channel signal was also determined with the HL-1 cells. Carbachol-induced changes in the DiBAC$_4$(3) signal were measured in Tyrode's solutions containing 1, 5, and 20 mM KCl. Under these conditions the reversal potential (E$_{rev}$) for the GIRK1/4 channel should follow E$_K$ and approach −120 mV and −50 mV in 1 mM and 20 mM KCl solutions, respectively. As shown in FIG. 4D, reducing the extracellular K$^+$ concentration ([K]$_o$) from 5 mM to 1 mM produced a two-fold increase in the carbachol-sensitive signal (mean=2.0±0.1, 3 plates). In contrast, increasing [K]$_o$ to 20 mM, which should shift E$_K$ close to the resting potential of the HL-1 cell (−50 to −65 mV), completely eliminated the carbachol-mediated decrease in the fluorescent signal.

Identification of GIRK1/4 Channel Blockers

Figure 5A:
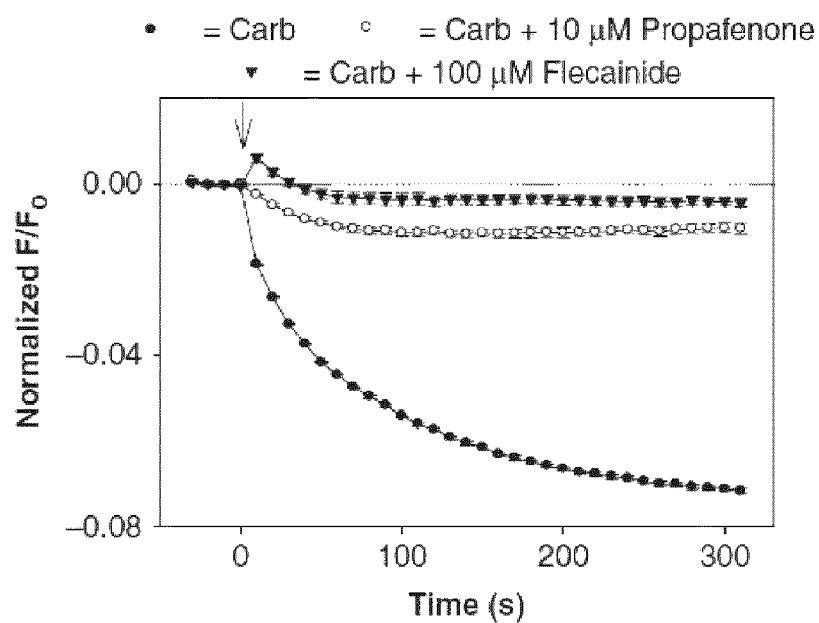
FIG. 5A illustrates a screen of anti-arrhythmic agents using the GIRK1/4 channel blocker assay with carbachol-sensitive fluorescent signal measured in cells pretreated for 5 min with drug vehicle solution (DMSO) (Carb) and either 10 µM propafenone or 100 µM flecanide (each point represents the mean±SE value obtained in 6 wells in one plate) in accordance with certain aspects of the present disclosure.
Figure 5B:
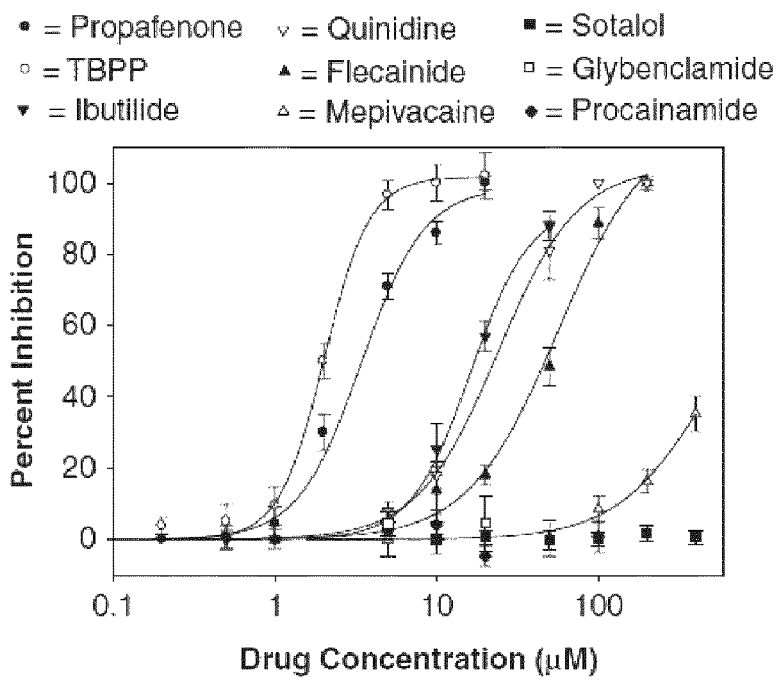
FIG. 5B illustrates a dose versus response curve for drug block of the carbachol signal (each point represents the mean±SE inhibition obtained from 3-5 experiments such as the one displayed in the top panel; calculated $IC_{50}$ values were TBPP=2 µM, propafenone=3 µM, ibutilide=16 µM, quinidine=24 µM and flecainide=56 µM; glybenclamide was not tested at concentrations >20 µM due to interference with the $DiBAC_4(3)$ fluorescence) in accordance with certain aspects of the present disclosure.

I$_{K,Ach}$ is blocked by several anti-arrhythmic drugs including propafenone, flecainide and amiodarone. Therefore, the GIRK1/4 channel assay was screened against a group of anti-arrhythmic agents. Propafenone was the most potent of the drugs tested with an IC$_{50}$ of 3 μM (FIGS. 5A-5B). This inhibitory potency was similar to that measured for propafenone block of the I$_{K,Ach}$ current (IC$_{50}$=2 μM) (FIGS. 2A-2C). Several structural analogs of propafenone were obtained from ChemBridge and tested for their inhibitory action. Of these compounds only 1-{2-[3-(tert-butylamino)-2-hydroxypropoxy]phenyl}-3-phenyl-1-propanone (TBPP) (IC$_{50}$=2 μM) was more potent than propafenone (FIGS. 5A-5B). Other anti-arrhythmic agents including ibutilide (IC$_{50}$=16 μM), quinidine (IC$_{50}$=24 μM) and flecainide (IC$_{50}$=56 μM) were also effective in inhibiting the carbachol-sensitive fluorescence signal. In contrast, drugs such as sotalol (blocker of the rapid component of the cardiac delayed rectifier K$^+$ channel), glybenclamide (ATP-sensitive K$^+$ channel blocker) and procainamide (voltage-gated Na$^+$ channel blocker) caused no block at the concentrations tested (FIGS. 5A-5B). Amiodarone, another anti-arrhythmic agent that blocks K$^+$ channels, was not evaluated since it interfered with the DiBAC$_4$(3) fluorescence at concentrations equal to or greater than 1 μM.

Figure 6A:
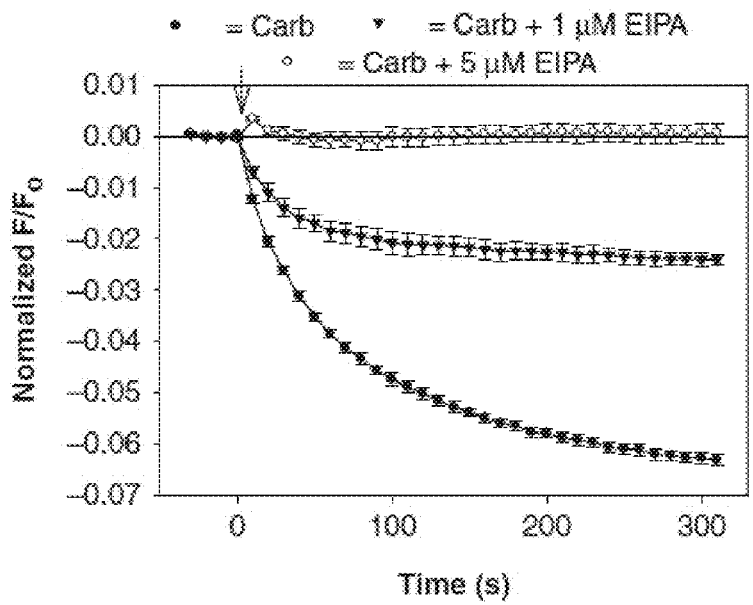
FIG. 6A illustrates a screen of amiloride analogs using the GIRK1/4 channel blocker assay with carbachol-sensitive fluorescent signal measured in cells pretreated for 5 min with drug vehicle solution (DMSO) (Carb) and either 1 µM or 5 µM 5-(N-ethyl-N-isopropyl)-amiloride (EIPA) (each point represents the mean±SE value obtained in 6 wells in one plate) in accordance with certain aspects of the present disclosure.
Figure 6B:
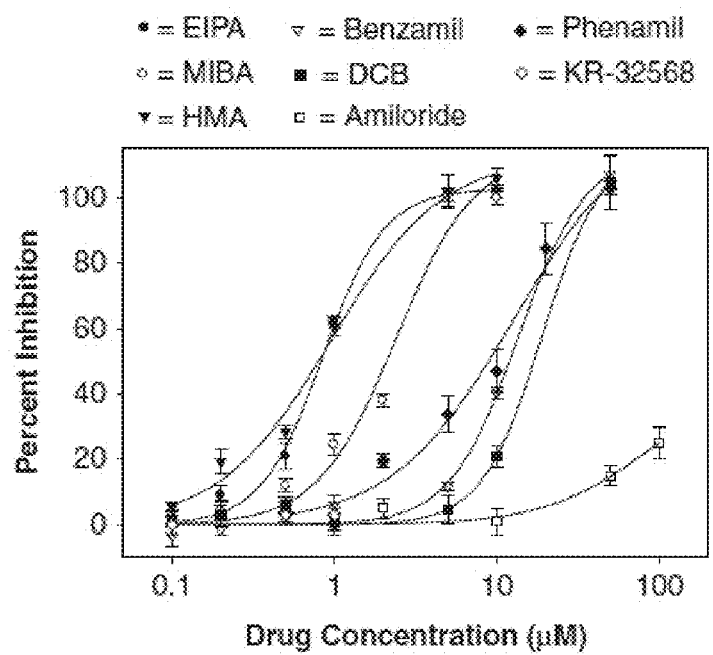
FIG. 6B illustrates dose versus response curve for drug block of the carbachol signal (each point represents the mean±SE inhibition obtained from 3-5 experiments such as the one displayed in the top panel; calculated $IC_{50}$ values were EIPA=0.8 µM, HMA=0.9 µM, 5-(N-methyl-N-isopropyl)-amiloride (MIBA)=2 µM, benzamil=13 µM, phenamil=13 µM and dichlorobenzamil (DCB)=20 µM. KR-32568 was not tested at concentrations >1 µM due to interference with the $DiBAC_4(3)$ fluorescence) in accordance with certain aspects of the present disclosure.

A small compound library, consisting of Na$^+$ and K$^+$ channel modulators (Sigma-Aldrich), was also tested using the GIRK1/4 channel assay. Several analogs of the epithelial Na$^+$ channel blocker amiloride were identified as inhibitors of the carbachol-sensitive signal when the modulators were screened at 1 μM. The full dose-response curves for these drugs are plotted in FIGS. 6A-6B. Both 5-(N-ethyl-N-isopropyl)-amiloride (EIPA) (IC$_{50}$=0.8 μM) and 5-(N,N-hexamethylene)-amiloride (HMA) (IC$_{50}$=0.9 μM) were effective at concentrations below 1 μM. In contrast, amiloride caused only a partial block at concentrations up to 100 μM (FIGS. 6A-6B). Since EIPA and HMA inhibit the Na$^+$/H$^+$ exchanger (NHE), the effect of the selective NHE inhibitor KR-32568 ([5-(2-methyl-5-fluorophenyl)furan-2-ylcarbonyl]guanidine) was determined in the assay. However, at drug concentrations up to 1 μM, KR-32568 caused no significant change in the carbachol-sensitive fluorescence (FIGS. 6A-6B).

Discussion

Expression of GIRK1/4 Channels in HL-1 Cells

The present disclosure demonstrates that immortalized cardiac HL-1 cells can be used for identifying new GIRK1/4 channel blockers. Consistent with the presence of the GIRK1/4 channel, HL-1 cells displayed a carbachol-activated Kir current and expressed the Kir3.1 channel subunit. Application of carbachol to cells loaded with a membrane potential-sensitive dye caused a rapid, time-dependent decrease in the fluorescent signal that was inhibited by BaCl$_2$ and muscarinic receptor antagonists. Finally, structural analogs of propafenone and amiloride were identified as GIRK1/4 channel blockers at concentrations less than 1 μM.

Development of a GIRK1/4 Channel Blocker Assay

The present disclosure developed a screening assay for identifying new GIRK1/4 channel blockers. For this purpose HL-1 cells were cultured in 96-well plates, loaded with the fluorescent membrane potential-sensitive indicator DiBAC$_4$(3) and stimulated with carbachol. Membrane potential-sensitive dyes have been utilized in drug discovery for a wide variety of ion channels including K$^+$, Na$^+$, hyperpolarization-activated cyclic-nucleotide gated and transient receptor potential channels. While fluorescent oxonol dyes, such as DiBAC$_4$(3), provide a convenient and inexpensive approach for measuring changes in membrane potential, they are limited by their slow response compared with electrophysiological measurements. In addition, oxonol dyes can be sensitive to changes in temperature and can be perturbed by test compounds. In the present disclosure, several drugs including glybenclamide (greater than 20 μM), KR-32568 (greater than 2 μM) and amiodarone (greater than or equal to 1 μM) reduced the DiBAC$_4$(3) fluorescence when tested under cell-free conditions. The use of several membrane potential probes, including oxonol dyes and fluorescence resonance energy transfer (FRET) dye systems, for measuring drug block of an endogenous Kir channel in RBL-2H3 cells has been evaluated. Although some compounds did produce oxonol dye interference when tested at concentrations greater than or equal to 10 µM, comparative $IC_{50}$ values for eight different Kir channel blockers were obtained using the different membrane potential probes. Alternate procedures, such as the thallium influx assay, can be used to identify GPCRs linked to GIRK channels.

Use of GIRK1/4 Blockers in Atrial Fibrillation

Atrial fibrillation (AF) is the most commonly occurring cardiac arrhythmia and is responsible for significant morbidity, mortality and health care costs. Several recent studies have identified $I_{K,Ach}$ as a novel therapeutic target for AF. However, the development of new and specific blockers of $I_{K,Ach}$ has been limited due to the absence of a cell-based screening assay for the GIRK1/4 channel. A number of anti-arrhythmic agents including amiodarone, flecainide and propafenone block $I_{K,Ach}$ in primary cultures of adult atrial myocytes. Consistent with this, the present disclosure describes that flecainide and propafenone blocked both the HL-1 cell $I_{K,Ach}$ and carbachol-sensitive fluorescent signal. For propafenone there was a good correlation between drug potency measured with the patch clamp procedure ($IC_{50}$=2 µM) and the FLIPR ($IC_{50}$=3 µM). The $IC_{50}$ values determined in the fluorescent assay for propafenone and flecainide ($IC_{50}$=56 µM) are consistent with the $IC_{50}$ values measured in primary cultures of guinea pig atrial myocytes (1 and 20 µM, respectively) using patch clamp analysis. As shown in FIGS. 6A-6B, three structural analogs of amiloride inhibited the carbachol-sensitive fluorescent signal at concentrations less than 1 µM. Acyl guanidine compounds such as EIPA, MIBA and HMA inhibit the $Na^{+/H+}$ exchanger (NHE). Thus these and chemically related drugs (cariporide, eniporide, etc.) may provide a good starting point for structure versus potency studies. Recently, two benzopyran derivatives, NIP-142 and NIP-151, were demonstrated to block GIRK channels expressed in HEK-293 cells at nanomolar concentrations. When tested in a canine model of AF, NIP-151 decreased atrial excitability and converted AF to sinus rhythm. While the selectivity of these agents for the GIRK family of IKr channels was not established, the results of these studies support the further development of new and selective GIRK1/4 channel blockers for the treatment of AF.

In the interests of brevity and conciseness, any ranges of values set forth in this specification are to be construed as written description support for claims reciting any sub-ranges having endpoints which are whole number values within the specified range in question. By way of a hypothetical illustrative example, a disclosure in this specification of a range of 1-5 shall be considered to support claims to any of the following sub-ranges: 1-4; 1-3; 1-2; 2-5; 2-4; 2-3; 3-5; 3-4; and 4-5.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only, and is not intended to limit the disclosure.

What is claimed is:

1. A method for determining an inhibitor of acetylcholine-activated potassium channel comprising:
    incubating a cardiac cell in a solution comprising a test compound and a compound to prevent calcium oscillations in the cardiac cell;
    adding a muscarinic (M2) receptor agonist to the cardiac cell in the solution;
    monitoring the cardiac cell for a change in membrane potential; wherein a statistically insignificant change in the membrane potential following addition of the muscarinic (M2) receptor to the solution signifies that the test compound is a $K^+$ channel blocker that inhibits opening of the acetylcholine-activated potassium channel.

2. The method according to claim 1, wherein the membrane potential is monitored by use of a detection substance that is capable of generating a detectable signal upon binding to a cytoplasmic component of the cardiac cell.

3. The method according to claim 2, wherein the detectable substance is a fluorescent membrane potential-sensitive dye.

4. The method according to claim 3, wherein the fluorescent membrane potential-sensitive dye is an oxonol dye.

5. The method according to claim 3, wherein the membrane potential is monitored by use of a fluorescent imaging plate reader.

6. The method according to claim 2, wherein the change in the membrane potential is determined by the ratio of the detectable signal following addition of the muscarinic (M2) receptor agonist to the cardiac cell in the solution to the detectable signal prior to addition of the muscarinic (M2) receptor agonist to the cardiac cell in the solution.

7. The method according to claim 1, wherein the muscarinic (M2) receptor agonist is acetylcholine.

8. The method according to claim 1, wherein the muscarinic (M2) receptor agonist is carbachol.

9. The method according to claim 1, wherein the cardiac cell is an atrial cell.

10. The method according to claim 9, wherein the atrial cell is an HL-1 cell.

11. The method according to claim 1, wherein the compound to prevent calcium oscillations in the cardiac cell is nisoldipine.

12. The method according to claim 1, wherein the solution includes the test compound in a concentration between 10 nanomolar and 10 micromolar.

13. The method according to claim 1, wherein the Z-factor of the method is between 0.5 and 1.

* * * * *